(12) United States Patent
Murphy et al.

(10) Patent No.: US 9,304,116 B2
(45) Date of Patent: Apr. 5, 2016

(54) CARTRIDGE WITH MULTIPLE ELECTROSPRAY EMITTERS

(75) Inventors: James P. Murphy, Franklin, MA (US); Joseph Michienzi, Plainville, MA (US)

(73) Assignee: Waters Technologies Corporation, Milford, MA (US)

( * ) Notice: Subject to any disclaimer, the term of this patent is extended or adjusted under 35 U.S.C. 154(b) by 252 days.

(21) Appl. No.: 14/004,969

(22) PCT Filed: Apr. 13, 2012

(86) PCT No.: PCT/US2012/033431
§ 371 (c)(1),
(2), (4) Date: Sep. 13, 2013

(87) PCT Pub. No.: WO2012/148699
PCT Pub. Date: Nov. 1, 2012

(65) Prior Publication Data
US 2014/0047907 A1    Feb. 20, 2014

Related U.S. Application Data

(60) Provisional application No. 61/478,713, filed on Apr. 25, 2011.

(51) Int. Cl.
*G01N 30/24*    (2006.01)
*G01N 30/60*    (2006.01)
(Continued)

(52) U.S. Cl.
CPC ............ *G01N 30/24* (2013.01); *G01N 30/6091* (2013.01); *H01J 49/0431* (2013.01);
(Continued)

(58) Field of Classification Search
CPC .............. G01N 30/24; G01N 30/6091; G01N 30/7233; H01J 49/0431; H01J 49/167; H01J 49/165; B01L 3/0268; B01L 3/50273; B01L 2200/0631; B01L 2400/0415
See application file for complete search history.

(56) References Cited

U.S. PATENT DOCUMENTS 5,969,353 A * 10/1999 Hsieh .................. H01J 49/0018
239/690
6,525,313 B1    2/2003 Park
(Continued)

FOREIGN PATENT DOCUMENTS

WO    2010102194 A1    9/2010

OTHER PUBLICATIONS

International Search Report and Written Opinion in international patent application No. PCT/US12/33431, mailed on Jul. 12, 2012; 7 pages.
(Continued)

*Primary Examiner* — Jack Berman
(74) *Attorney, Agent, or Firm* — Schmeiser, Olsen & Watts LLP

(57) ABSTRACT

An apparatus includes a portable housing and a plurality of separately operable microfluidic emitters disposed within the housing. Each microfluidic emitter h an inlet for receiving a liquid and an outlet for emitting a spray. Each microfluidic emitter is movable within the portable housing between a first position in which the outlet of that microfluidic emitter is fully retracted within the portable housing and a second position in which the outlet of that microfluidic emitter projects out of the portable housing. The portable housing with the multiple emitters is adapted to be detachably coupled to another housing portion. This housing portion includes a microfluidic substrate with a channel for transporting an eluent and an outlet aperture for emitting the eluent. The inlet of one of the emitters is detachably coupled to the outlet aperture of the microfluidic substrate.

15 Claims, 9 Drawing Sheets

(51) Int. Cl.
- *H01J 49/16* (2006.01)
- *H01J 49/04* (2006.01)
- *G01N 30/72* (2006.01)
- *B01L 3/02* (2006.01)
- *B01L 3/00* (2006.01)

(52) U.S. Cl.
CPC ............. *H01J49/167* (2013.01); *B01L 3/0268* (2013.01); *B01L 3/50273* (2013.01); *B01L 2200/0631* (2013.01); *B01L 2400/0415* (2013.01); *G01N 30/7233* (2013.01)

(56) References Cited

U.S. PATENT DOCUMENTS

| | | | |
|---|---|---|---|
| 6,800,849 B2 | 10/2004 | Staats | |
| 7,105,810 B2 | 9/2006 | Karneoke et al. | |
| 7,179,423 B2 | 2/2007 | Bohm et al. | |
| 7,265,347 B2* | 9/2007 | Guevremont | H01J 49/0018 250/281 |
| 7,439,499 B2* | 10/2008 | Bailey | H01J 49/0431 250/285 |
| 7,557,342 B2 | 7/2009 | Federov et al. | |
| 8,753,586 B2* | 6/2014 | Prentice | B01L 3/563 137/315.01 |
| 9,095,791 B2* | 8/2015 | Prentice | B01L 3/563 |
| 2002/0000517 A1 | 1/2002 | Corso et al. | |
| 2002/0110902 A1* | 8/2002 | Prosser | G01N 35/0099 435/287.1 |
| 2003/0224531 A1 | 12/2003 | Brennan et al. | |
| 2006/0099116 A1 | 5/2006 | Manger et al. | |
| 2009/0045333 A1 | 2/2009 | Chiarot et al. | |
| 2014/0217196 A1* | 8/2014 | Prentice | G01N 30/6052 239/3 |
| 2014/0319042 A1* | 10/2014 | Prentice | B01L 3/563 210/198.2 |

OTHER PUBLICATIONS

International Preliminary Report on Patentability in counterpart international patent application No. PCT/US2012/033431, mailed on Nov. 7, 2013; 6 pages.

Extended European Search Report in related U.S. Patent Application No. 12777623.5, mailed on Dec. 8, 2014; 6 pages.

Extended European Search Report in counterpart European Patent Application No. 12777623.5, mailed on Apr. 8, 2015; 9 pages.

* cited by examiner

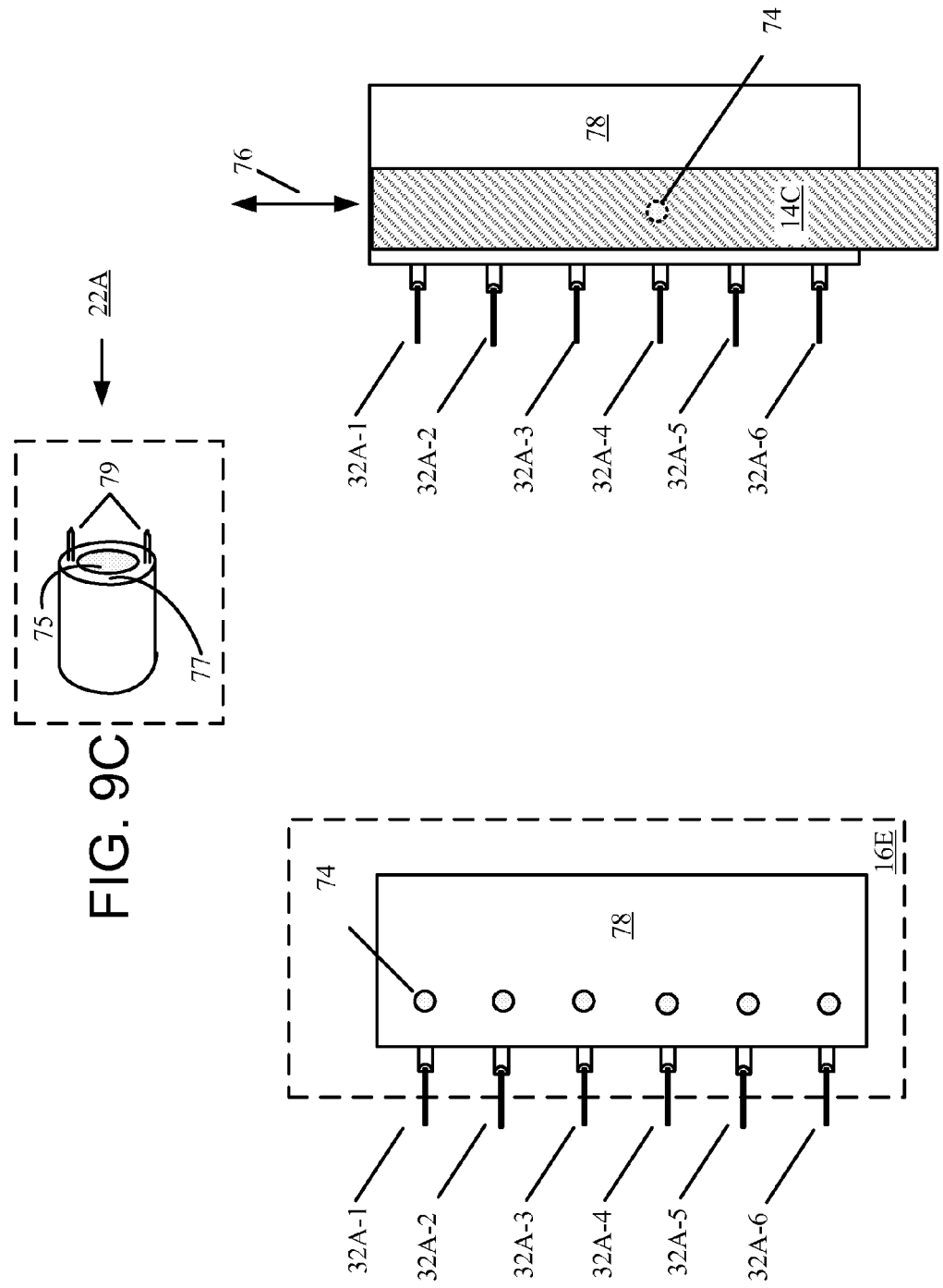

CARTRIDGE WITH MULTIPLE ELECTROSPRAY EMITTERS

RELATED APPLICATION

This application claims the benefit of and priority to co-pending U.S. provisional application No. 61/478,713, filed Apr. 25, 2011, titled "Cartridge with Multiple Electrospray Emitters," the entirety of which is incorporated by reference herein.

FIELD OF THE INVENTION

The invention relates generally to liquid chromatography mass-spectrometry instruments. More specifically, the invention relates to multiple emitter interfaces to a microfluidic substrate used by such analytical systems.

BACKGROUND

High-performance liquid chromatography (HPLC) instruments are analytical tools for separating, identifying, and quantifying compounds. In a typical liquid chromatography analysis, a pump takes in and delivers a mixture of liquid solvents to a sample manager, where the material under analysis, called the sample, awaits injection into the solvents. The sample is the material under analysis. Examples of samples include complex mixtures of proteins, protein precursors, protein fragments, reaction products, and other compounds, to list but a few. The mobile phase, comprised of a sample dissolved in a mixture of solvents, moves to a point of use, such as a column, referred to as the stationary phase. By passing the mobile phase through the column, the various components in the sample separate from each other at different rates and thus elute from the column at different times.

The separation techniques of a liquid chromatography (LC) system are often used in combination with one or more additional analysis techniques to produce multidimensional information about a sample. For example, mass spectrometry (MS) can provide molecular weight and structural information. A difficulty associated with combining disparate techniques occurs at the interface between the techniques. For example, the combination of liquid chromatography and mass spectrometry requires effective transport of the sample eluent produced by the liquid chromatography system to the mass spectrometry instrument for analysis. Industry has devised various ionization techniques to achieve this sample eluent transport, including field desorption, thermospray, and electrospray. When used in conjunction with liquid chromatography techniques, many consider electrospray (ESI) to be the ionization method of choice. For electrospray ionization, a union couples the liquid chromatography column to an ESI emitter. A clogged or poorly performing ESI emitter, however, will produce poor data quality and will reduce the productivity of the LC-MS system until the ESI emitter is replaced.

SUMMARY

In one aspect, the invention features an apparatus comprising a portable cartridge housing including a first housing portion detachably coupled to a second housing portion. The first housing portion includes a microfluidic substrate with a channel for transporting an eluent and an outlet aperture for emitting the eluent. The second housing portion has a plurality of spray units. Each spray unit has an inlet for receiving the eluent, a lumen through which the eluent travels, and an outlet for emitting a spray of the eluent. A first one of the spray units housed within the second housing portion being in fluidic communication with the outlet aperture of the microfluidic substrate.

In another aspect, the invention features an apparatus comprising a portable housing, adapted to detachably couple to a cartridge containing a microfluidic substrate, and a plurality of separately operable microfluidic emitters disposed within the housing. Each microfluidic emitter has an inlet for receiving a liquid and an outlet for emitting a spray. Each microfluidic emitter is movable within the portable housing between a first position in which the outlet of that microfluidic emitter is fully retracted within the portable housing and a second position in which the outlet of that microfluidic emitter projects out of the portable housing in response to the portable housing being coupled to the cartridge with the microfluidic substrate.

In yet another aspect, the invention features a method replacing a electrospray emitter in a liquid chromatography system that uses a cartridge having a first housing portion detachably coupled to a second housing portion, the first housing portion including a microfluidic substrate with a channel for transporting an eluent and an outlet aperture for emitting the eluent, and the second housing portion having a plurality of electrospray emitters. The method comprises decoupling the second housing portion from the first housing portion, wherein the decoupling removes fluidic communication between an inlet of a first one of the electrospray emitters and an outlet aperture of the microfluidic substrate. After decoupling the second housing portion from the first housing portion, an orientation of the second housing portion relative to the first housing portion is changed such that an inlet of a second one of the electrospray emitters is aligned with the outlet aperture of the microfluidic substrate. After changing the orientation of the second housing portion relative to the first housing portion, the second housing portion is coupled to the first housing portion such that the inlet of the second one of the electrospray emitters is brought into fluidic communication with the outlet aperture of the microfluidic substrate.

In still yet another aspect, the invention features an apparatus comprising a portable housing adapted to detachably couple to a cartridge containing a microfluidic substrate and a multilayer structure disposed within the portable housing. The multilayer structure provides a plurality of microfluidic emitters. Each microfluidic emitter has an inlet opening for receiving a liquid, a channel through which the liquid travels, and an outlet orifice for emitting a spray.

BRIEF DESCRIPTION OF THE DRAWINGS

The above and further advantages of this invention may be better understood by referring to the following description in conjunction with the accompanying drawings, in which like numerals indicate like structural elements and features in various figures. The drawings are not necessarily to scale, emphasis instead being placed upon illustrating the principles of the invention.

FIG. 9A and FIG. 9B are end views of a linear multiple-emitter emitter case and a substrate housing coupled to the linear-emitter emitter case, respectively, and FIG. 9C is a coupling mechanism for guiding the coupling of the multiple-emitter emitter case 16E to the substrate housing according to another embodiment of a microfluidic cartridge.

DETAILED DESCRIPTION

Microfluidic cartridges described herein contain multiple spray emitters situated in-line with a microfluidic substrate. At least one of the emitters is operatively connected to an outlet of the microfluidic substrate from which to receive liquid for spraying. An emitter case contains the emitters and is adapted for connection to and disconnection from a frame that houses the microfluidic substrate. The emitter case facilitates the quick replacement of an emitter that is performing poorly or becoming clogged. When an emitter in use becomes clogged, the emitter case can be decoupled from the substrate housing, reoriented to align a different emitter with the outlet of the microfluidic substrate, and then reconnected. This replacement of an emitter may be performed manually by a person or automatically by a mechanical and/or computer-driven mechanism. Quick replacement of a malfunctioning emitter effectively reduces the down time of the LC-MS instrument.

Figure 1:
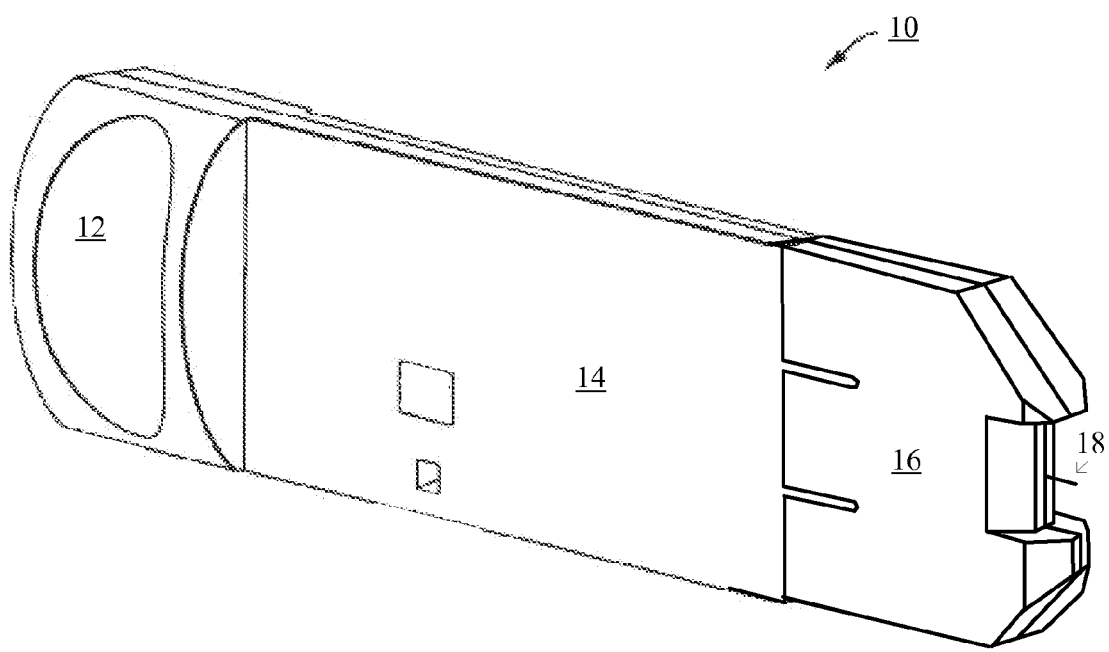
FIG. 1 is an isometric view of an embodiment of a microfluidic cartridge having a substrate housing and an emitter case, the substrate housing containing a multilayer substrate with one or more liquid chromatography columns, and the emitter case housing a plurality of spray emitters.

FIG. 1 shows an embodiment of a microfluidic cartridge 10 that houses a microfluidic substrate having one or more LC columns and a plurality of electrospray emitters. At least one of the LC columns is operatively coupled to one of the electrospray emitters. This embodiment of microfluidic cartridge 10 has a grip end 12, a microfluidic substrate housing 14, and an emitter case 16, which houses a plurality of electrospray emitters, as described herein. The emitter case 16 is deemed "in-line" with the LC column and is detachable from the rest of the microfluidic cartridge 10. In this embodiment, a spray tip 18 of one of the emitters extends from one end of the emitter case 16. The orifice of the emitter tip can be in the range of microns to nanometers in diameter. That the spray tip 18 extends from the emitter case 16 is an indication that its emitter is operatively coupled to an outlet of the microfluidic substrate.

Housed within the substrate housing 14 of the microfluidic cartridge is a substantially rigid, ceramic-based, multilayer fluidic substrate (not shown). A channel formed in the layers of the substrate operates as a separation column. Multiple separate channels, each serving as a different separation channel, may be formed. Apertures in the side of the substrate provide openings into each channel through which fluid may be introduced into the column. Fluid passes through the apertures under high pressure and flows toward the emitter coupled at the egress end of the channel. Openings in the side of the substrate housing 14 provide fluidic inlet ports for delivering fluid to the microfluidic substrate.

The microfluidic cartridge 10 is adapted for insertion into an installation chamber of an HPLC instrument. When installed in the chamber, a mechanical clamping force urges the microfluidic substrate against fluidic nozzles coupled to the installation chamber. In addition, the spray tip 18 of the emitter is brought into operable communication with mass spectroscopy components of the HPLC instrument. The nozzles deliver fluid to the microfluidic substrate through the fluidic inlet ports of the substrate housing 14. From the column of the substrate, the separated fluid leaves the cartridge through the spray tip 18. One example implementation of the microfluidic cartridge 10 can be found in PCT application No. PCT/US2010/026342, titled "Electrospray Interface to a Microfluidic Substrate," filed on Mar. 5, 2010 and published on Sep. 10, 2010 as International publication No. WO 2010/102194 A1, the entirety of which is incorporated by reference herein.

Figure 2:
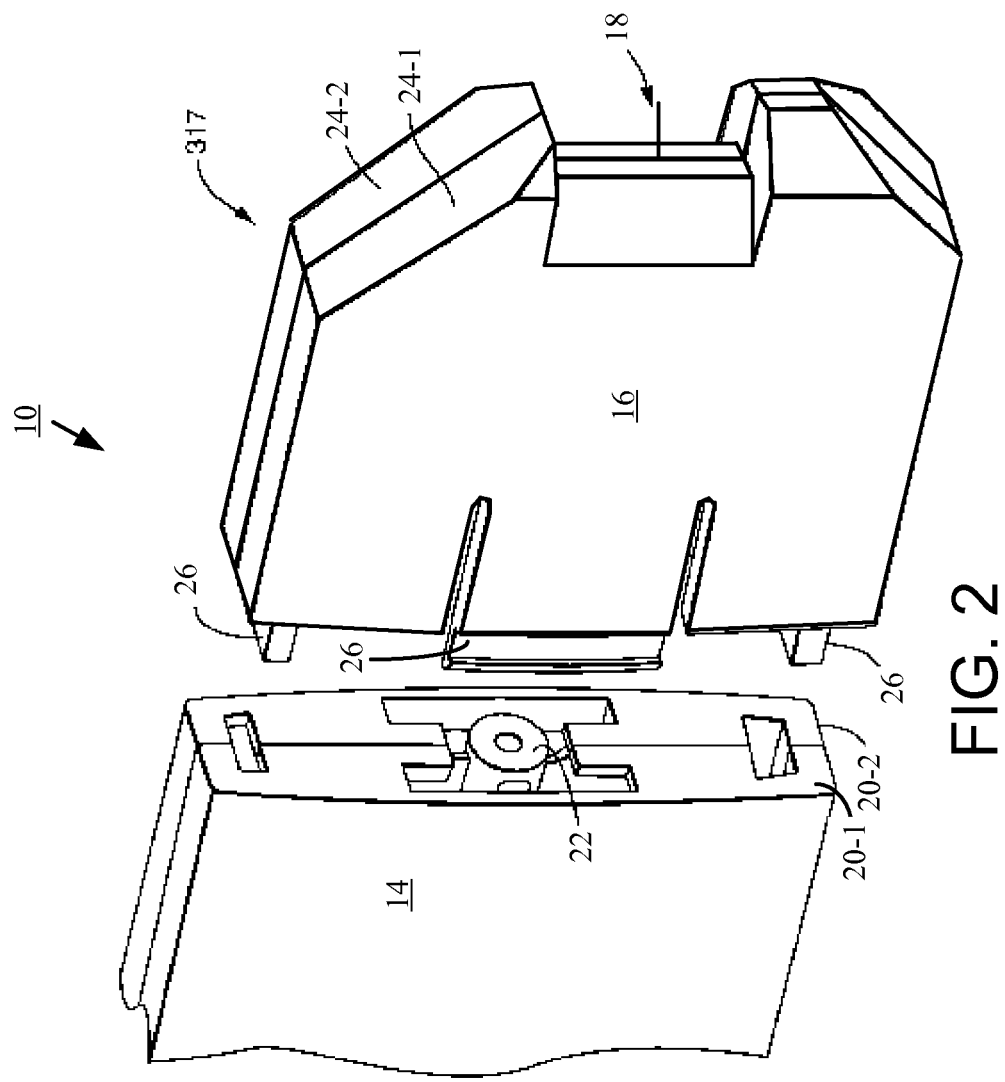
FIG. 2 is an exploded view of another embodiment of the microfluidic cartridge showing the emitter case as detached from the substrate housing.

FIG. 2 shows another embodiment of the microfluidic cartridge 10 showing the emitter case 16 as detached from the substrate housing 14. The detachability provides relative ease in swapping and/or replacing the emitter case, while retaining most or all other microfluidic components of the cartridge. The substrate housing 14 has left and right housing portions 20-1, 20-2 and holds a retainer 22. Although shown to lie in a same plane as the end of the substrate housing, in some embodiments, the retainer 22 can extend beyond the substrate housing's end. The emitter case 16 has left and right housing portions 24-1, 24-2, which define a spray-tip protection feature, namely a bracket that surrounds the tip 18 (the tip does not extend beyond the foremost edge of the protection feature). The left and right housing portions 24-1, 24-2 have latch features 26 for connecting the emitter case 16 to the substrate housing 14. The latch features 26 allow for detaching the emitter case 16 from the substrate housing 14 when changing emitters, as described herein. Other embodiments can use any suitable attaching features, for example, screws, clips, and magnets.

Figure 3:
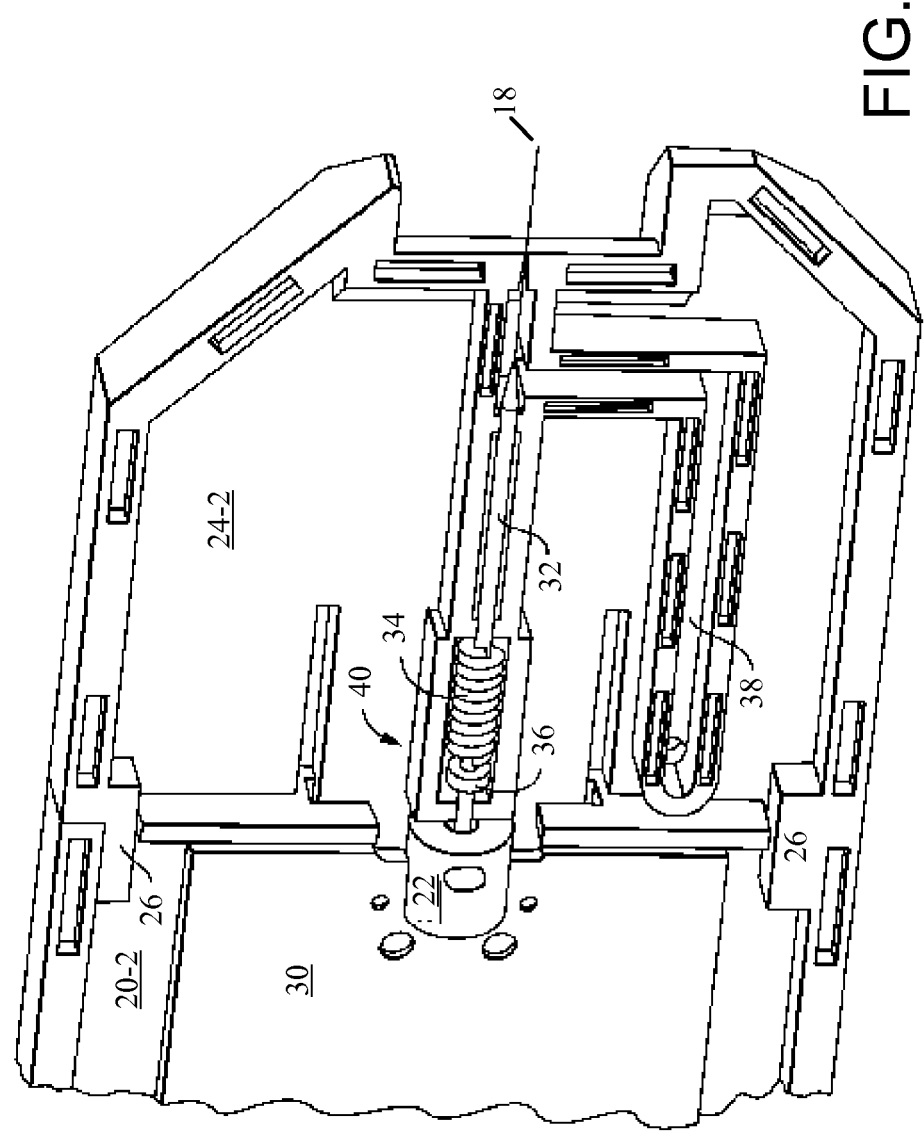
FIG. 3 is a side view of the microfluidic cartridge of FIG. 2 with one side of its housings removed to reveal various components housed with the substrate housing and the emitter case.

FIG. 3 shows the microfluidic cartridge 10 with the right housing portions 20-1, 24-1 removed to reveal various components housed with the substrate housing 14 and the emitter case 16. Within the substrate housing 14 is the retainer 22 and a multilayer microfluidic substrate 30 coupled at one edge to the retainer 22. Formed within the multilayer substrate 30 is an LC column with an egress end that opens at the edge near the retainer 22. The substrate 30 has a recessed edge portion 56 (FIG. 4) for receiving the retainer 22. A recessed edge is optionally used, for example, to produce a desirably smooth edge near the orifice and/or to protect the orifice portion of the edge.

Housed within the emitter case 16 are one emitter 32, a spring 34, and a fitting 36, which secures the spring 34 to the emitter 32. (The emitter case of FIG. 3 has but one emitter 32, illustrating the various features and general functional principles of each emitter in an emitter case that has multiple emitters.) The spring 34 wraps around a portion of the length of the emitter 32 and is disposed within a compartment 40 sized to hold the spring 34. The inlet end of the emitter 32 enters an opening in the retainer 22. The retainer 22 operates to align a lumen of the emitter 32 with the outlet aperture of the microfluidic substrate 30. The compartment 40 operates as a spring-retaining feature that secures the spring 34 and applies a force to the spring 34 when the detachable emitter case 16 is attached to the substrate housing 14. Connection produces a face seal between the inlet end of the emitter 32 and the outlet aperture of the microfluidic substrate 30. Preferably, additional component(s) urge the emitter 32 into contact with the substrate 30 with sufficient force to provide a greater interfacial pressure than the pressure of eluent flowing out of the column from the outlet port of the substrate 30. Additionally, interior walls of the left housing portion 24-2 define a gas passageway 38 for delivery of a gas to surround the spray tip 18.

Figure 4:
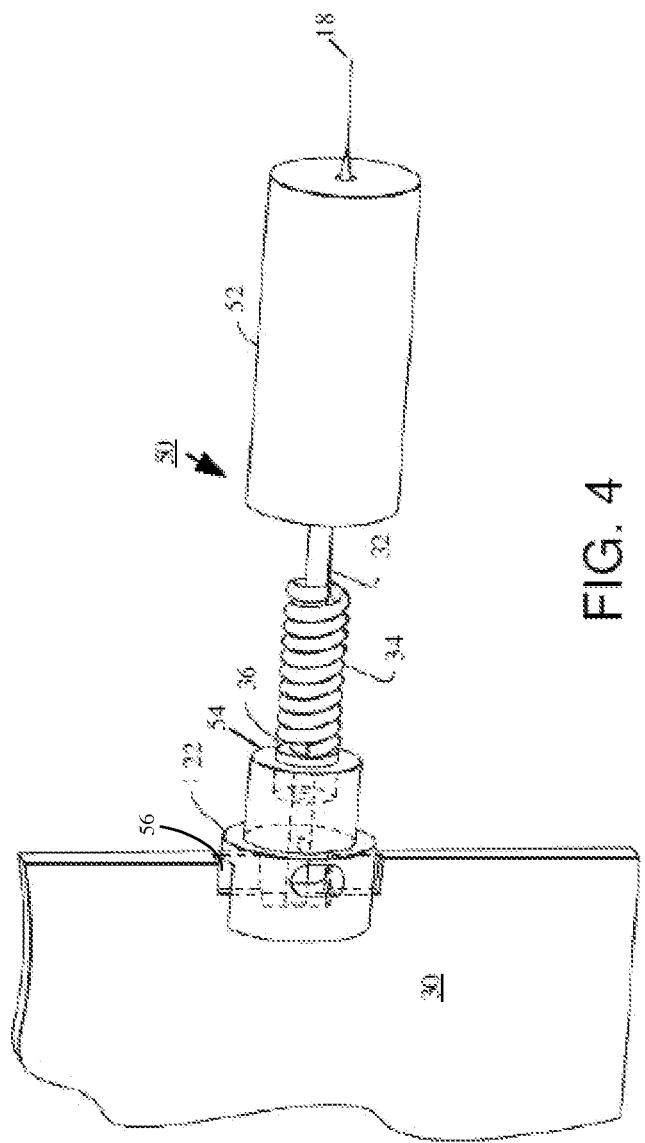
FIG. 4 is a side view of a spray unit comprising a single emitter.

FIG. 4 shows an embodiment of a spray unit 50 that can be used in a microfluidic cartridge 10. As used herein, the term "spray unit" is a descriptive convenience not intended to limit the spray unit to any specific set of components or to limit the location of such components. Preferably, the spray unit 50 is defined as only those components associated with the emitter case 16, although some of the components can reside in the substrate housing 14 whereas other components of the spray unit 50 can reside in the emitter case 16. In this embodiment, the spray unit 50 includes the emitter 32, spring 34, fitting 36, and a fixed or removable retainer cap 52. When the spray unit 50 is assembled for operation, the spring 34 and fitting are covered by the cap 52 (that is, from where it appears in FIG. 4, the cap 52 slides over the spring 34 and fitting 36 to abut the end of the retainer 22). Instead of the compartment 40 of FIG. 3, this embodiment of spray unit 50 employs a surface 54 to apply a force to the spring 34 when the detachable emitter case 16 is attached to the substrate housing 14.

Figure 5:
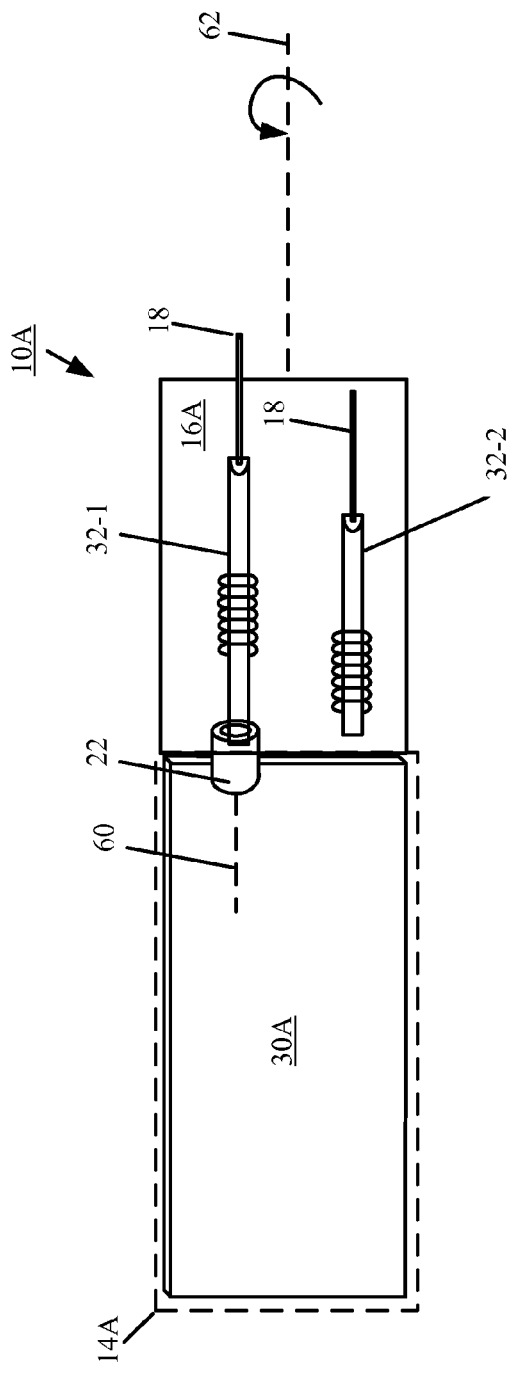
FIG. 5 is a side view of a microfluidic cartridge having a multiple-emitter emitter case coupled to a substrate housing.

FIG. 5 shows an embodiment of a microfluidic cartridge 10A having an emitter case 16A with multiple emitters, one of which is coupled to a microfluidic substrate 30A housed within a substrate housing 14A. The various details of the housing portions of the microfluidic cartridge 10A are omitted from FIG. 5 to focus the description on the salient features. The omitted details are functionally similar to those described in connection with FIG. 2-4, requiring some structural modifications within the ability of those of ordinary skill in the art to accommodate the particular embodiments of emitter case 16A, substrate housing 14A, and microfluidic substrate 30A.

In this embodiment, the multiple-emitter emitter case 16A has two emitters 32-1, 32-2 (with accompanying springs, fittings, tips, etc.). One emitter 32-1 is coupled at one end to a retainer 22. This coupling produces a fluidic path from a column 60 formed in a multilayer substrate within the substrate housing 14A to the tip 18 of the emitter 32. The act of coupling the emitter case 16A to the substrate housing that contains the microfluidic substrate 30A causes the tip 18 to project from the emitter case 16A, thereby placing the tip 18 into operational position. The other emitter 32-2 is in a retracted position, its tip 18 remaining within the emitter case 16A. The retracted position is the default position of each emitter 32-1, 32-2 before the emitter case 16A is coupled to the microfluidic substrate 30A.

By having multiple emitters within the microfluidic cartridge 10A, one emitter can serve as a convenient replacement for the other after the other emitter ceases to function satisfactorily. For example, the emitter 32-2 can be the replacement of emitter 32-1. To make the replacement, the emitter case 16A is decoupled from the substrate housing sufficiently far to break the face seal between the emitter-in-use 32-1 and the outlet aperture of the microfluidic substrate 30A. Decoupling causes the first emitter 32-1 to retract within the emitter case 16A. The emitter case 16A is then rotated 180 degrees about the axis 62, and reconnected to the substrate housing 14A, the inlet end of the emitter 32-2 entering the retainer 22 and making a face seal with the microfluidic substrate 30A. The location of the retainer 22 is offset from the midpoint of the edge of the substrate housing 14A so that the retainer 22 will be in alignment with one emitter or the other, depending upon the particular orientation of the emitter case 16A when attached to the substrate housing 14A. Reconnecting causes the tip of the other emitter 32-2 to project from the emitter case 16A, placing it into operational position. The replacement can be an automated or manual process, a process performed by an LC/MS instrument in which the microfluidic cartridge 10A is installed or by person. An automated process can also maintain track of which emitters or spray units in the emitter case 10A have already been used, and notify a user when no replacement emitters are available.

Figure 6:
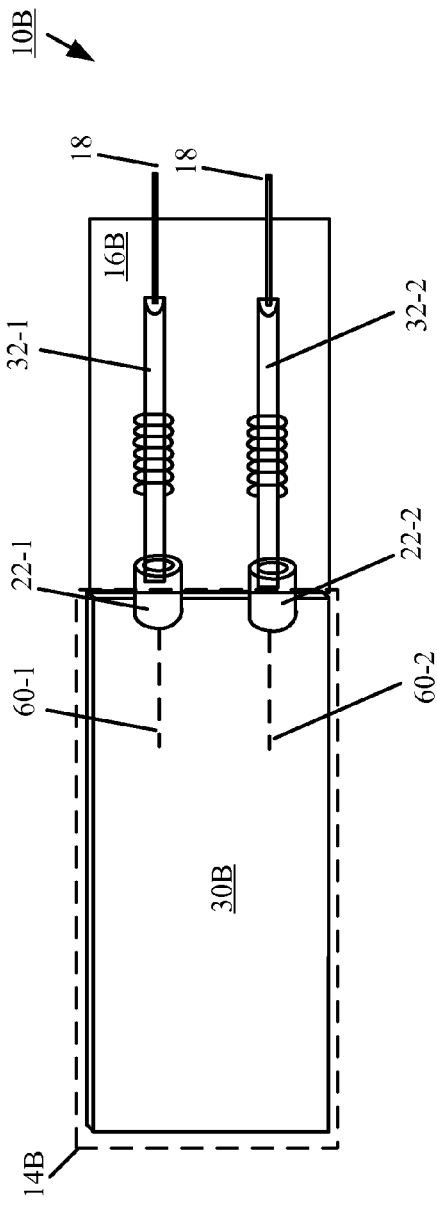
FIG. 6 is a is a side view a microfluidic cartridge having a multiple-emitter emitter case coupled to a substrate housing, each emitter being coupled to a different liquid chromatography column formed in a substrate within the substrate housing.

FIG. 6 is another simplified view, this one of another embodiment of a microfluidic cartridge 10B having a multiple-emitter emitter case 16B coupled to a substrate housing 14B that houses a multilayer substrate 30B within which are multiple separately operable columns 60-1, 60-2. The substrate housing 14B also has a pair of retainers 22-1, 22-2 (generally, 22), which are symmetrically offset from the midpoint of the edge of the substrate housing 14B. The multiple-emitter emitter case 16B has two emitters 32-1, 32-2 (generally, emitter 32) like the emitter case 16A of FIG. 5. Each emitter 32 is coupled at its inlet end to one of the retainers 22-1, 22-22. Coupling the emitter case 16B to the substrate housing 14B causes the emitters 32 to the project from the emitter case 16B, placing both emitters 32 into operational position. The coupling of the multiple-emitter emitter case 16B to the substrate housing 14B may be reversible; meaning that emitter 32-1 can be coupled to either retainer 22-1 or to retainer 22-2 (with emitter 32-2 being coupled to the other retainer). Embodiments of this emitter case 16B may or may not be detachable from the substrate housing 14B. Having multiple emitters within the microfluidic cartridge 10B, one coupled to a different column in the substrate housing 14B, permits concurrent operation of multiple columns Further, an operator also has the option of using one emitter-column combination as a spare for when the other emitter-column combination becomes unusable (e.g., clogged from use).

Figure 7A:
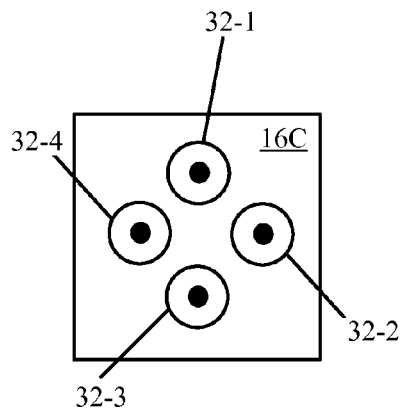
FIG. 7A and FIG. 7B are end views of another embodiment of a microfluidic cartridge having a multiple-emitter emitter case coupled to a substrate housing, FIG. 7A being an end view of the emitter case, and FIG. 7B being an end view of the substrate housing coupled to the emitter case.
Figure 7B:
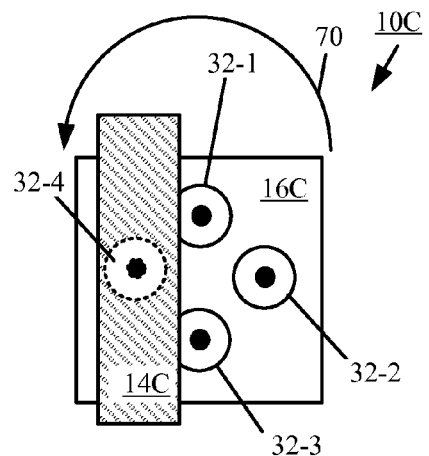
Figure 7C:
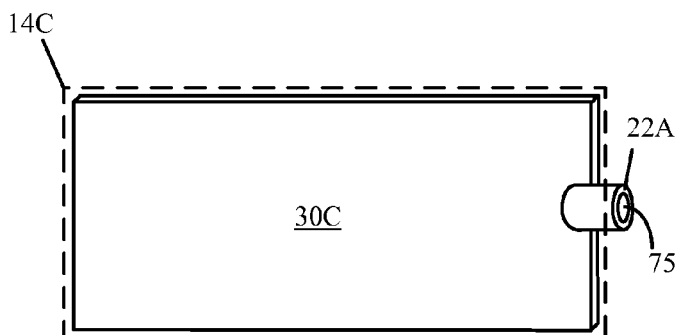
FIG. 7C is a side view of a substrate housing having a retainer disposed centrally along its edge.

FIG. 7A and FIG. 7B show another embodiment of a microfluidic cartridge 10C having a multiple-emitter emitter case 16C coupled to a substrate housing 14C shown in FIG. 7C. FIG. 7A is an end view of the emitter case 16C, and FIG. 7B is an end view of the substrate housing 14C coupled to the emitter case 16C. FIG. 7C shows the substrate housing 14C having a connector mechanism 22A (here, similar to retainer 22 of FIG. 5) disposed approximately midpoint on the edge facing the emitter case 16C, although other locations along the edge are also usable. The outlet aperture of the microfluidic substrate 30C is aligned with an outlet aperture 75 of the connector mechanism 22A. Again, the various details of the housing portions of the microfluidic cartridge 10C are omitted to focus the description on salient features.

In FIG. 7A, the emitter case 16C has four emitters 32-1, 32-2, 32-3, and 32-4 (generally, 32), their inlets being arranged at the four points of a compass. Other embodiments can have three or greater than four of such emitters. Herein, the arrangement pattern formed by the inlets is abstractly referred to as polygonal; that is, if lines were drawn to connect the emitter inlets, the produced pattern has three (i.e., triangular) or more sides.

In FIG. 7B, the substrate housing 14C is aligned with and coupled to the emitter 32-4. The inlet end of the emitter 32-4 enters the outlet aperture 75 of the connector mechanism 22A and produces a face seal with the outlet aperture of the microfluidic substrate 30C. In this configuration, the emitters 32-1, 32-2, and 32-3 are unused and available as replacements. When unused, the emitters are in a retracted position, similar to that shown in FIG. 5. To effect a replacement, the emitter case 16C is decoupled from the substrate housing 14C, rotated 90 degrees (like a barrel as illustrated by arrow 70), and then reconnected to the substrate housing 14C. The replacement can be an automated or manual process.

Figure 8A:
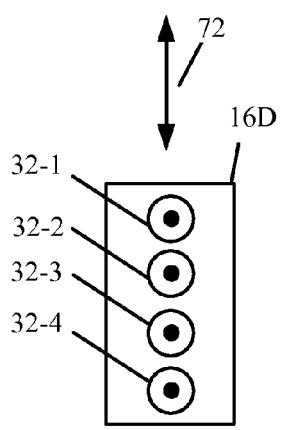
FIG. 8A and FIG. 8B are end views of another embodiment of a microfluidic cartridge having a linear multiple-emitter emitter case coupled to a substrate housing, FIG. 8A being an end view of the emitter case, and FIG. 8B being an end view of the substrate housing coupled to the emitter case.
Figure 8B:
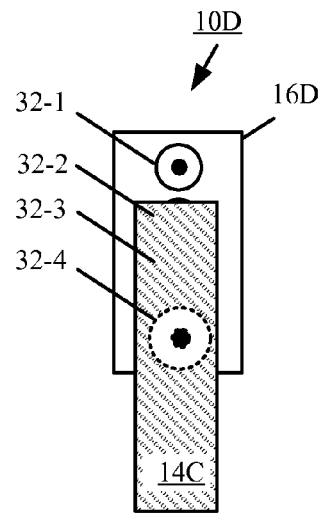

FIG. 8A and FIG. 8B show another embodiment of a microfluidic cartridge 10D having a multiple-emitter emitter case 16D coupled to a substrate housing 14C (FIG. 7C). FIG. 8A is an end view of the emitter case 16D and FIG. 8B is an end view of the substrate housing 14C coupled to the emitter case 16D. The emitter case 16D has four emitters 32-1, 32-2, 32-3, and 32-4 (generally, 32) in a linear arrangement running north and south. In an alternative embodiment, the linear arrangement of emitters can run east and west. In FIG. 8B, the substrate housing 14C is aligned with and coupled to the emitter 32-4. The inlet end of the emitter 32-4 enters the outlet aperture 75 of the connector mechanism 22A and produces a face seal with the outlet aperture of the microfluidic substrate 30C. In this configuration, the emitters 32-1, 32-2, and 32-3 are unused and available as replacements. When unused, the emitters are in a retracted position, similar to that shown in FIG. 5. To execute a replacement, the emitter case 16D is decoupled from the substrate housing 14C, indexed or stepped down (or up) one or more positions, as indicated by arrow 72, and then reconnected to the substrate housing 14C. The decoupling breaks the face seal of the emitter-in-use and withdraws the inlet end of the emitter entirely out of the connector mechanism 22A, out far enough to permit the stepping of the emitter housing 16D. The replacement can be an automated (computer-driven mechanism) or manual process.

FIG. 9A and FIG. 9B show another embodiment of a microfluidic cartridge 10E having a multiple-emitter emitter case 16E coupled to a substrate housing 14C (FIG. 7C). FIG. 9A is an end view of the emitter case 16E containing a linear strip 78 of emitters and FIG. 9B is an end view of the substrate housing 14C coupled to the emitter case 16E. The connector mechanism 22A has an outlet aperture 75 that is in fluidic communication with the outlet aperture of the microfluidic substrate housed within the substrate housing 14C. In this embodiment, the face 77 (FIG. 9C) of the connector mechanism 22A provides the leak proof face seal, as described in more detail below. The connector mechanism 22A can also include alignment pins 79 situated about the outlet aperture 75 for guiding the coupling of the multiple-emitter emitter case 16E to the substrate housing 14C, as is generally known to those of ordinary skill in the art.

In this embodiment, the linear emitter strip 78 has six emitters 32A-1, 32A-2, 32A-3, 32A-4, 32A-5, and 32A-6 (generally, 32A) in a linear-strip arrangement running north-south. Although only a single linear column of emitters is shown, another embodiment can have a second linear column of emitters adjacent the first column, with the emitters of that second linear column extending in the opposite direction as those of the first column. The linear emitter strip 78 has an opening 74 for each of the emitters 32A that provides an inlet port to that emitter 32A, and pin holes (not shown) next to each opening 74 to receive the pins 79 of the connector mechanism 22A. The emitter case 16E has corresponding openings aligned with these openings 74; such emitter-case openings can help to align the connector mechanism 22A and the outlet aperture 75 of the substrate housing 14C with a given opening 74 when connecting the substrate housing to the emitter case 16E. From its respective opening 74, the lumen of each emitter 32A bends generally orthogonally to project from the side of the emitter case 16E. In contrast to the emitters 32 of FIGS. 8A and 8B, which have lumens that will be coaxial with respect to the outlet aperture of the microfluidic substrate when the emitter case 16E and substrate housing 14C are joined, the emitters 32A are orthogonal. (In another embodiment, the lumens or channels of the emitters 32A can extend coaxially from the inlet openings 74 of the emitters 32A, to extend from the other side opposite the substrate housing 14C.)

For example, FIG. 9B shows the substrate housing 14C aligned with and coupled to the emitter 32A-4. The face 77 of the connector mechanism 22A produces a face seal around the opening 74 of the emitter 32A-4. The other emitters 32A-1, 32A-2, 32A-3, 32A-5, and 32A-6 in this configuration are unused and available as replacements. To execute a replacement, the emitter case 16E is decoupled from the substrate housing 14C, stepped down (or up) one position as indicated by arrow 76, and then reconnected to the substrate housing 14C. Instead of moving the emitter case 16E, the substrate housing 14C can be stepped up or down. The replacement can be an automated or manual process.

The emitter case 16E can be manufactured and marketed as a separate consumable adapted for connecting to a given substrate housing, and as a dispensable consumable after all of the emitters have been used. The linear strip of emitters 32A housed within the emitter case 16E can be constructed with a material particularly suited for making a face seal with the face 77 of the substrate housing 14C. Examples of such materials include polyimide, PEEK, and VESPEL®. The resulting linear-strip 78 of emitters 32A has flexibility characteristics similar to those of a flex-circuit.

Figure 10:
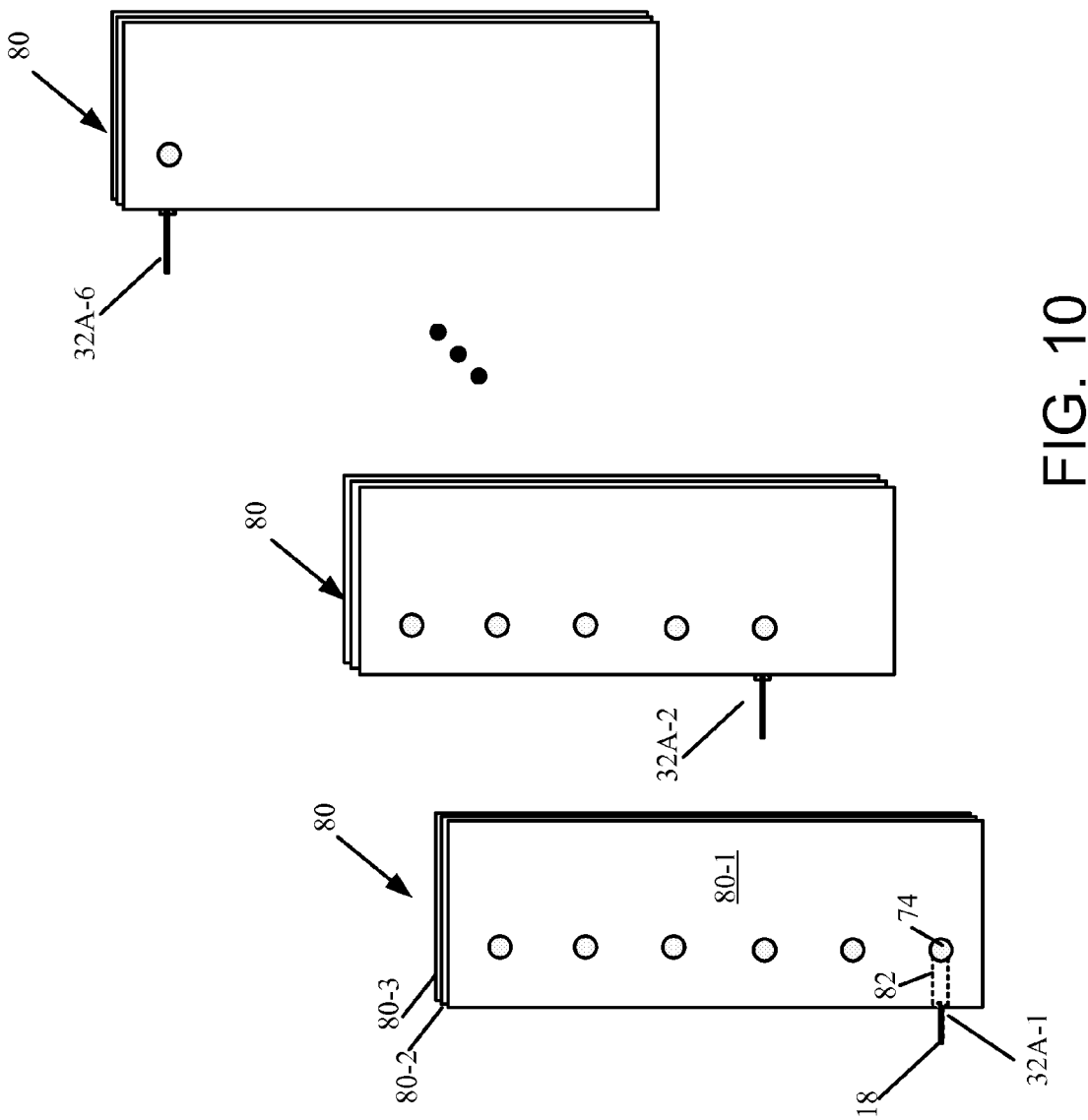
FIG. 10 is a diagram illustrating a simplified multi-layer construction of the emitter case of FIG. 9A and FIG. 9B.

FIG. 10 illustrates a simplified construction of the linear emitter strip 78 of FIG. 9A and FIG. 9B. The linear emitter strip 78 is constructed of layers 80 of a polymeric material, for example, PEEK or of metal, for example, titanium. Multiple of such layers 80 can be used to construct each emitter 32A. For example, a first layer 80-1 can have an inlet port (opening 74) behind which a next layer 80-2 has a lateral channel 82 formed therein, the channel 82 extending to and opening at the side edge of the layer 80-2 and the inlet port 74 opening into one end of the channel 82. An emitter tip 18 is formed from the edge of the layer 80-2, at the channel opening. A third layer 80-3 of material sandwiches the channel layer 80-2 between it and the first layer 80-1. The first layer 80-1 also has openings for each inlet port of the other emitters 32A to be constructed. The other emitters 32A can be similarly constructed. A heating and curing process combines all of the layers.

Figure 11B:
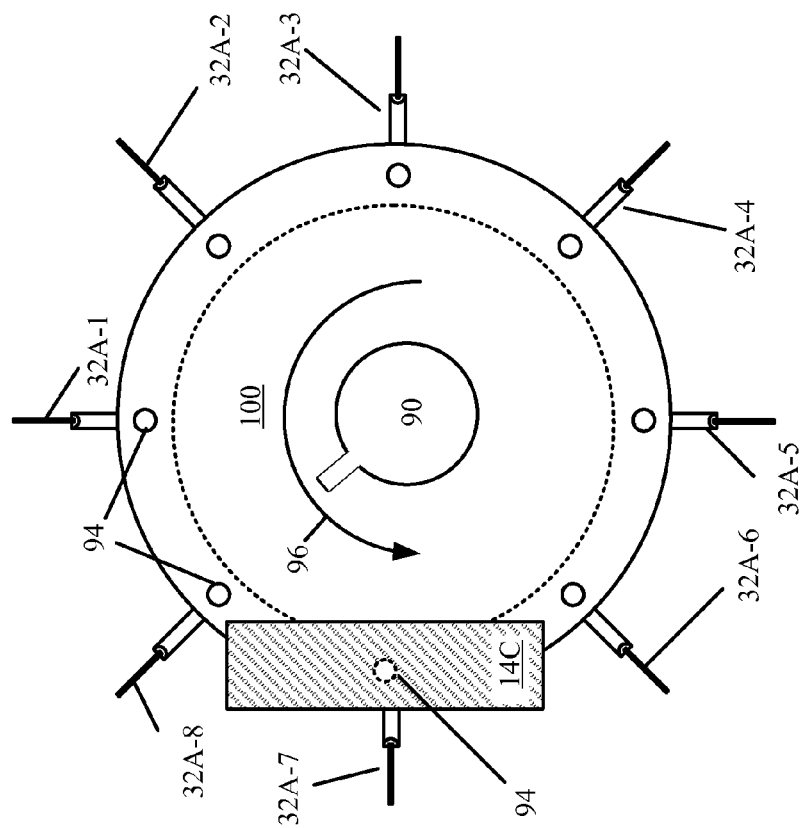
FIG. 11A and FIG. 11B are diagrams of another embodiment of a microfluidic cartridge having a wheel-shaped multiple-emitter emitter case.
Figure 11A:
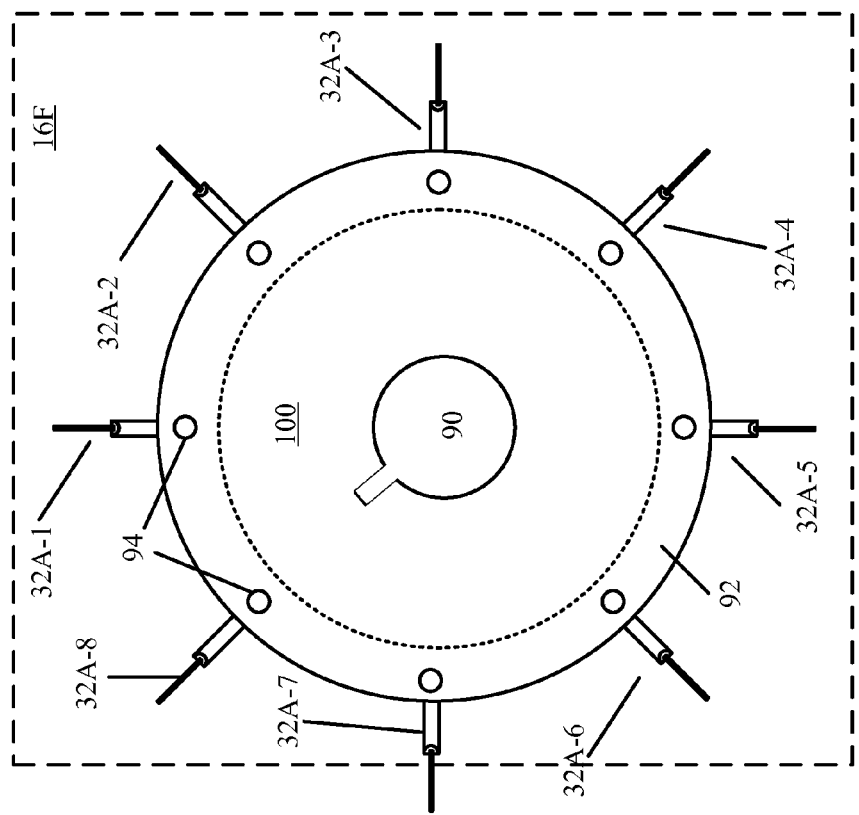

FIG. 11A and FIG. 11B show another embodiment of a microfluidic cartridge 10F having a multiple-emitter emitter case 16F, which houses a wheel 100 of emitters, coupled to a substrate housing 14C (FIG. 7C). FIG. 11A is an end view of the emitter case 16F having eight emitters 32B-1, 32B-2, 32B-3, 32B-4, 32B-5, 32B-6, 32B-7, and 32B-8 (generally, 32B) extending from the edge of the circumference of the emitter case 16F. The emitter wheel 100 also has opening 94 that serves as an inlet port to each of the emitters 32B. (The emitter case 16F has corresponding openings aligned with these openings 94; such emitter-case openings can help to align the outlet aperture 75 of the substrate housing 14C with a given opening 94 when connecting the substrate housing to the emitter case.) The lumen of each emitter 32B turns generally orthogonally from its respective opening 94 and extends to the circumferential edge of the emitter case 16F. Accordingly, the lumens of the emitters 32B are primarily orthogonal to the 75 aperture of the substrate housing 14C. (In another embodiment, the lumens or channels of the emitters 32B can extend coaxially from the inlet openings 94 of the emitters 32B and extend from the other side opposite the substrate housing 14C.) The emitter case 16F can also have a keyed opening 90 in its center, for use by a mechanical mechanism to turn the emitter case 16F like a dial when stepping or indexing from one emitter 32B to the next.

The wheel 100 of emitters can be constructed of a polymeric material, for example, PEEK, or of a metal, for example, titanium. If constructed of polymeric material, the wheel 100 of emitters can have flexibility characteristics similar to those of a flex-circuit, and can establish an effective the leakproof face seal with the face 77 of the substrate housing. If constructed of metal, the emitter wheel 100 preferably includes a polymeric gasket 92 that surrounds the openings 94 and produces the leak-proof face seal around the outlet aperture 75 of the substrate housing 14C with which the gasket 92 comes into contact. Alternatively, the sealing material can be disposed on the face 77 of the substrate housing 14C around the outlet aperture 75, which comes into contact with the metal around the opening 94 of the emitter and produces the face seal. Like the emitter case 16E of FIG. 9A and FIG. 9B, the emitter case 16F can be manufactured and marketed as a separate consumable adapted for connecting to a given substrate housing and dispensable after all its emitters have been used.

FIG. 11B shows the substrate housing 14C aligned with and coupled to the emitter 32B-7, as an example. The other emitters 32B-1, 32B-2, 32B-3, 32B-5, 32B-6, and 32B-8 are unused in this configuration and available as replacements. To execute a replacement, the emitter case 16F is decoupled from the substrate housing 14C, rotated clockwise or counter-clockwise by one or more positions, as indicated by arrow 96, and then reconnected to the substrate housing 14C. The rotation can be performed in automated fashion or be a manual process. Construction of the emitter wheel 100 can be achieved in multi-layer fashion similar to that of the linear emitter strip described in connection with FIG. 10.

Reference in the specification to "one embodiment" or "an embodiment" means that a particular, feature, structure or characteristic described in connection with the embodiment is included in at least one embodiment of the teaching. The appearances of the phrase "in one embodiment" in various places in the specification are not necessarily all referring to the same embodiment.

While the invention has been shown and described with reference to specific preferred embodiments, it should be understood by those skilled in the art that various changes in form and detail may be made therein without departing from the spirit and scope of the invention as defined by the following claims.

What is claimed is:

1. An apparatus, comprising:
  A portable cartridge including a first housing portion detachably coupled to a second housing portion, the first housing portion including a microfluidic substrate with a channel for transporting an eluent and an outlet aperture for emitting the eluent, the second housing portion having a plurality of spray units, each spray unit having an inlet for receiving the eluent, a lumen through which the eluent travels, and an outlet for emitting a spray of the eluent, the inlet of one of the spray units housed within the second housing portion being in fluidic communication with the outlet aperture of the microfluidic substrate, wherein the spray unit that is in fluidic communication with the outlet aperture of the microfluidic substrate extends from the second housing portion while each other spray unit is retracted within the second housing portion and is available as a spare spray unit.

2. The apparatus of claim 1, wherein the microfluidic substrate includes a second channel for transporting an eluent and a second outlet aperture for emitting the eluent transported by the second channel, and wherein a second one of the spray units housed within the second housing portion is in fluidic communication with the second outlet aperture of the microfluidic substrate.

3. The apparatus of claim 1, wherein the inlets of the spray units are at a coupling end of the second housing portion such that the inlet of the first spray unit becomes oriented for fluidic communication with the outlet aperture of the microfluidic substrate when the second housing portion couples to the first housing portion in a first orientation and the inlet of a second spray unit becomes oriented for fluidic communication with the outlet aperture of the microfluidic substrate when the second housing portion couples to the first housing portion in a second orientation.

4. The apparatus of claim 3, wherein the microfluidic substrate has an edge that faces the second housing portion, the outlet aperture being on the edge of the microfluidic substrate at a location offset from a midpoint along the edge.

5. The apparatus of claim 3, wherein the microfluidic substrate has an edge that faces the second housing portion, the outlet aperture being on the edge of the microfluidic substrate at a midpoint along the edge.

6. The apparatus of claim 3, wherein the inlets of the plurality of spray units are oriented linearly at the coupling end of the second housing portion.

7. The apparatus of claim 3, wherein the inlets of the plurality of spray units present a polygonal pattern at the coupling end of the second housing portion.

8. The apparatus of claim 1, wherein the lumen of the first spray unit coupled to the outlet aperture extends generally orthogonally from the inlet of the first spray unit.

9. The apparatus of claim 1, wherein the second housing portion is a rotary device and the outlets of the spray units extend radially from a circumferential edge of the rotary device.

10. The apparatus of claim 1, further comprising mechanical means for automated changing which one of the spray units is presently coupled to the outlet aperture of the microfluidic substrate.

11. An apparatus comprising:
  a portable housing adapted to detachably couple to a cartridge containing a microfluidic substrate; and
  a plurality of microfluidic emitters disposed within the portable housing, each microfluidic emitter having an inlet for receiving a liquid and an outlet for emitting a spray, each microfluidic emitter being movable within the portable housing between a first position in which the outlet of that microfluidic emitter is fully retracted within the portable housing and a second position in which the outlet of that microfluidic emitter projects out of the portable housing in response to the portable housing being coupled to the cartridge with the microfluidic substrate.

12. The apparatus of claim 11, wherein the inlets of the plurality of emitters are oriented linearly at a coupling end of the portable housing.

13. The apparatus of claim 11, wherein the inlets of the plurality of emitters present a polygonal pattern at a coupling end of the portable housing.

14. The apparatus of claim 11, wherein a lumen of each emitter extends generally orthogonally from the inlet of that emitter.

15. The apparatus of claim 11, wherein the portable housing is a rotary device and the outlets of the emitters extend radially from a circumferential edge of the rotary device.

* * * * *